United States Patent [19]
Lindh

[11] Patent Number: 6,165,228
[45] Date of Patent: Dec. 26, 2000

[54] FOOT PROSTHESIS

[75] Inventor: Leif Lindh, Danderyd, Sweden

[73] Assignee: Pro-Pel AB, Danderyd, Sweden

[21] Appl. No.: 09/214,420

[22] PCT Filed: Jul. 4, 1997

[86] PCT No.: PCT/SE97/01220

§ 371 Date: Feb. 5, 1999

§ 102(e) Date: Feb. 5, 1999

[87] PCT Pub. No.: WO98/01092

PCT Pub. Date: Jan. 15, 1998

[30] Foreign Application Priority Data

Jul. 5, 1996 [SE] Sweden ................................. 9602676

[51] Int. Cl.[7] .................................................. A61F 2/66
[52] U.S. Cl. .............................................................. 623/55
[58] Field of Search ........................................ 623/53–56

[56] References Cited

U.S. PATENT DOCUMENTS

| 5,116,384 | 5/1992 | Wilson et al. | 625/53 |
| 5,139,525 | 8/1992 | Kristinsson | 623/55 |
| 5,290,319 | 3/1994 | Phillips | 623/55 |
| 5,514,185 | 5/1996 | Phillips | 623/54 |
| 5,695,527 | 12/1997 | Allen | 623/55 |
| 5,888,239 | 3/1999 | Wellershaus et al. | 625/55 |

*Primary Examiner*—Bruce Snow
*Attorney, Agent, or Firm*—Young & Thompson

[57] ABSTRACT

An adaptable forefoot part for use in a foot prosthesis, wherein the forefoot part is adapted to be used together with a prosthesis socket, and an elongated support part, wherein the forefoot part (13) has a fastening part (20) with at least one fastening element (41,42) adapted to be attached to the support part (11), an adaptable and resilient intermediate part (15) and a front part (19). The invention also relates to a foot unit comprising an adaptable forefoot part, wherein a heel part (12) is attached to the fastening part (20) and the fastening part placed on a support part (11) with a fastening element (41), as well as a system intended for individually adaptable foot prostheses, wherein an adaptable forefoot part according to the invention, a heel part, a support part and an outer casing of predetermined size can be combined in order to provide one adapted for the user.

6 Claims, 2 Drawing Sheets

FOOT PROSTHESIS

CROSS REFERENCE TO RELATED APPLICATION

This is the 35 USC 371 National Phase of International application PCT/SE97/01220 filed on Jul. 4, 1997 which designated the United States of America.

FIELD OF THE INVENTION

The invention relates to a forefoot pail intended to be comprised in a foot means adapted to cooperate with a support part comprised in a foot prosthesis, and a foot means comprising a combined heel part and forefoot part for fastening onto the support part.

BACKGROUND OF THE INVENTION

Foot prostheses of different types are known. The prostheses are usually designed so that an ordinary shoe can be used on the prosthesis. At a certain heel height, which can be adjusted during manufacturing of the prosthesis adapted to an individual. the prosthesis feels comfortable to walk on and to load, but without a shoe or with a different heel height the prosthesis is no longer comfortable to use since the angle of the foot with respect to the ground is no longer correct.

The most common solution to the above problem is to either angle the whole foot prosthesis downwards and forwards, or to lower the heel part when, for example, one is to walk without a shoe. Angling the prosthesis downwards does not produce an anatomically correct foot shape, i.e. one does not achieve the type of foot shape which is necessary during the use of a higher heel, and if alternatively the heel part is lowered, this instead results in a lengthening of the leg which will cause discomfort, especially in the back.

WO93/24080 (same applicant) describes the general design of a foot prosthesis with a support part and a foot means which cooperates with the support part, wherein the foot means comprises a forefoot part arranged so that it is slidably fixed to the support part in its axial direction and separately a heel part intended to be arranged at the lower end of the support part.

SE-B-8504225-5 a foot prosthesis is described having a central part which supports the sole, heel and leg parts. In this prosthesis the heel is movably arranged in relation to the central part of the prosthesis and to the part of the sole of the foot which is fixedly joined with the central part. Movement of the heel is obtained by the latter being connected with the rear part of the central part by means of a bar which can be locked in a hole in said part and which in the unlocked position is displaceable in relation to the central part for adjusting the heel in relation to the foot sole. In this device a lengthening of the leg is obtained by the hole being moved downwards in relation to a reference point, e.g. the knee of the user.

U.S. Pat. No. 4,547,913 describes a completely different solution to the problem. Here the prosthesis is made of three rigidly connected parts, the leg part, the foot part and the heel part made of fibre reinforced resin, where the material and design of the parts gives flexibility to the prosthesis.

In U.S. Pat. No. 5,181,933 is described a prosthesis foot comprising essentially two curvilinear parts of which one extends from the attachment part to the toe part of the foot. Halfway at between the two ends and underneath the first curvilinear part a second curvilinear part is attached in such a way as to provide the heel part of the foot prostheses.

In FR C 907 306 a prosthesis foot is described, in which the foot-part and the toes are separated by an opening. The parts are connected through a number of steel bands. The foot and the toe part are also connected through a damper comprising a cylinder and a piston and the damper connected to the foot and the toe part respectively.

In DE C 841 192 another foot prostheses is described which comprises a foot prostheses having a toe part which may be bent. The two parts are connected through a bendable sole and are also connected via a flexible elongated rubber piece extending into two holes in the two parts respectively.

These three prostheses comprise a prostheses foot which is complete in the sense of the forefoot and the heel being directly connected to each other.

U.S. Pat. No. 5,181,933 is described a prosthesis foot comprising essentially two curvilinear parts of which one extends from the attachment part to the toe part of the foot. Halfway between the two ends and underneath the first curvilinear part a second curvilinear part is attached in such a way as to provide the heal part of the foot prostheses.

In FR,C,907 306 a prosthesis foot is described, in which the foot-part and the toes are separated by a opening. The parts are connected through a number of steel bands. The foot and the toe part are also connected through a damper comprising a cylinder and a piston and the damper connected to the foot and the toe part respectively.

In DE,C,8411.92 another foot prostheses is described which comprises a foot prostheses having a toe part which may be bent. The two parts are connected through a bendable sole and is also connected via a flexible elongated rubber piece extending into two holes in the two parts respectively.

These three prostheses comprise a prostheses foot which is complete in the sense of the fore foot and the heal being directly connected to each other.

During the production of foot and leg prostheses a number of factors have to be taken into account. The normal foot can move in all planes, individually or in combination. The lower leg of a person consists of two bones which by cooperation with each other and with the ankle joint permit a rotational movement, torsion of the lower leg, which continues in a rotation of the foot. Furthermore, the calf muscles of the lower leg provide a variable pushing off force, i.e. adapted for the specific purpose, There are today technical solutions for solving this problem to some extent, e.g. in SE-B-8201389-7, where the foot prosthesis consists of a continuous hollow core, which is secured directly onto the leg prosthesis adapter and which by virtue of its design, with rigid and elastic region provides mobility in the dorsal plantar direction. The foot however, does not have any capacity for energy storage, it has no adjustable heel and it is not made from a light but strong composite mateial.

Moreover, in the natural foot an adjuscent of the attitude of the heel takes place when the height of the heel increases. This can be illustrated most clearly through observing the movement which takes place when the foot is being introduced into a shoe or when walking on tiptoe. What happens is that the muscles on the back of the lower leg contract and in this way the heel is lifted, while at the same time as the heel is lifted an angling of the forefoot takes place in the case of a normal walking movement. The higher the heel is lifted, the greater is the angle obtained between the forefoot and the adjoining part of the foot.

SUMMARY OF THE INVENTION

An object of the invention is to provide an improved forefoot part to a foot prosthesis or an improved foot means.

Another object of the invention is an improved forefoot part of a foot prosthesis which can be rigidly or slidably attached onto a support part.

A further object of the invention is to provide a forefoot part which is easy to adapt to an individual who is using the prosthesis.

Another object is to provide a forefoot part to the type of prosthesis which is described in the preamble so that a variable starting force is achieved.

Yet another object is to provide a certain torsion capacity in the forefoot so that the prosthesis will be comfortable to use and will have a physiologically correct shape.

Another object is to make it possible to exchange forefoot parts adapted for special conditions.

A further object is to be able to adapt the size of the adaptable forefoot part and to be able to use the forefoot part in both a left and a right prosthesis.

A further object is to provide a system for producing foot prostheses of different sizes and left and right variants of these.

A further object of the invention is to avoid the above mentioned problems of the prior art foot prostheses and in this way provide a a prosthesis which always is comfortable for the user, independent of the heel height, and which can satisfy varying demands on the starting force of the user of the prosthesis.

These objects are achieved through the features stated in the independent claims. Preferred embodiments have the features which are mentioned in the subclaims.

In order to provide the desired elasticity and adaptability of the characteristics of the prosthesis depending on use and user of the prosthesis, the forefoot part of the prosthesis is made of three distinct parts: a rigid part, a resilient and/or adaptable intermediate part and a front part. Before adaption to the individual the parts can be completely separate. The adaptable and resilient part can, however, be permanently fixed to one of the two other parts.

According to the invention the problem with resilience and torsion capacity in the forefoot part is solved through a special construction of the intermediate part. The intermediate part according to the invention is formed of at least one elongated element wherein the first end of this or these elongated elements are intended to be fastened to the fixed part and the other end of this or these elongated elements to be fastened to the front part.

The forefoot part according to the invention can be used both in a prosthesis in which the forefoot is permanently fastened to the support part and in adjustable foot prostheses, in which the forefoot part can be adjusted in height by being slidably attached to the support part. The forefoot part can thereafter be manually adjusted and locked into place in many ways, e.g. by using bolts or the like, or can be moved by means of a motor which is operatively connected to the forefoot part, wherein the motor itself when stationary forms a stop.

The foot means, forming a combination of the forefoot part and a heel part according to the invention, can be used together with a support part of normal construction.

A special advantage of the forefoot part and the foot means according to the invention is that the constituent parts after adaption to the individual are provided with suitable cosmetics, i.e. an outer casing which then forms the complete prosthesis together with the forefoot part and the heel part. This means that with the help of a system containing only a few parts it is possible to produce foot prostheses of different sizes and of left and right shape. These foot prostheses are subsequently provided with a cosmetic adapted to the right size, viz. a casing which looks like a normal foot.

BRIEF DESCRIPTION OF THE DRAWINGS

The invention is described in more detail below with reference to the accompanying drawings where.

DESCRIPTION OF THE PREFERRED EMBODIMENTS

Figure 1:
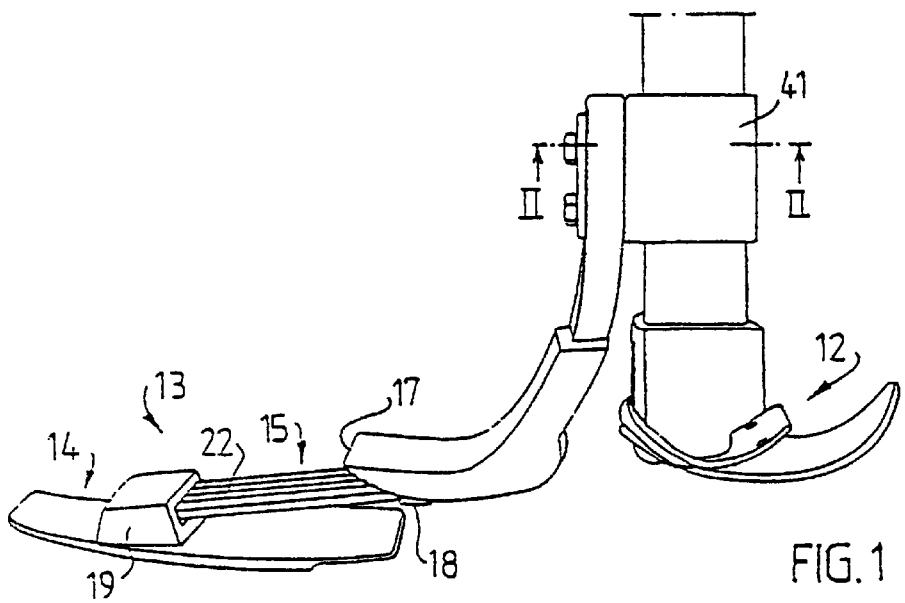
FIG. 1 shows an embodiment of a foot means according to the invention fixed to a support part on the foot prosthesis.

FIG. 1 shows a prosthesis equipped with a foot means comprising a forefoot part according to the invention. The prosthesis has a prosthesis socket 10, a tube 11 (support part), a heel part 12 and a forefoot part 13. The tube 11 is preferably formed of a normal standard tube of the type which is normally used for fastening prosthesis feet into prosthesis sockets and which can be said to be a replacement either completely or partially for the lower leg. The forefoot part 13 is arranged in a movable way on the tube which below is referred to as the support part 11, and a heel part 12 is arranged on the lower end of the support part 11.

In this embodiment the support part 11 is shown as a tube with a circular cross-section. which is the most common shape for this part. This, however, does not mean that the support part used in the invention could not have some other cross-section, such as e.g. quadratic, triangular or oval etc.

The forefoot part 13 comprises a front part 14, an intermediate par 15 and a fastening part 20. The intermediate part 15 forms the part of the forefoot part which is specially shaped in order to be individually adaptable to the individual who uses the prosthesis. In order to achieve this, the intermediate part 15 is arranged in the shape of elongated resilient elements 22, which have a circular, oval or rectangular cross-section. This makes it possible to adjust the stiffness, torsion, the resilient ability and the give in the forefoot part.

In one embodiment the intermediate part can be formed of a single element.

The ability to adjust the elasticity in the forefoot part is important as the wearers of the prostheses can have a wide spread of weights and foot sizes and, in addition, different types of activities place different requirements on the elastic characteristics of the forefoot part. The element 22 is fixed to the front part 14 so that the element 18 is permanently or removably attached to a holder 19. The second end of the element is fastened (not shown) under the fastening part 20. The holders can be constructed in such a way that the elements can be partially introduced through the holder and thereafter cut off to the right length and thereafter fastened in a permanent way to the holders and in this way to the fastening part 20.

It is important for the strength of the forefoot part that the elongated elements 18 introduced into the holder, which is mounted under the fastening part 20, are fixed in such a way, and that the end of the fastening part 20, under which the holder 18 is mounted, is so shaped that no sharp bending of the elements occurs at the front edge 17 of the fastening part. The front part of the fastening part 20 therefore has a gently bent profile in order to allow the elements to yield.

Figure 2:
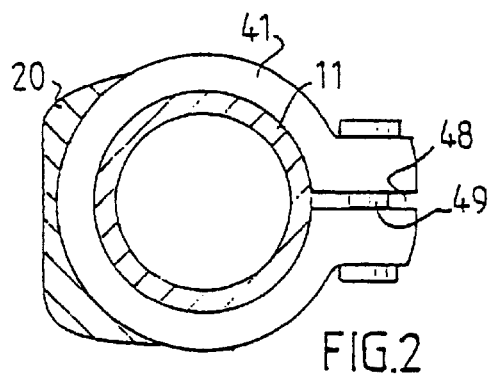
FIG. 2 shows a cross-section through the fastening means of a further embodiment of the forefoot part.

FIG. 2 shows the cross-section along the line 11—11 in FIG. 1 in a first embodiment. A fastening element, the annular part 41 of the fastening part 20, can be seen surrounding the support part 11. The fastening part 20 is also visible. The fastening element 41 has an opening 48 which can be closed with a bolted joint 49 which is shown on the drawing. The method for closing the annular part 41 and locking it around the support part 11 is not important as long as the fastening element 41 and the forefoot part 13 remain in the predetermined position along the support part 11.

Figure 3:
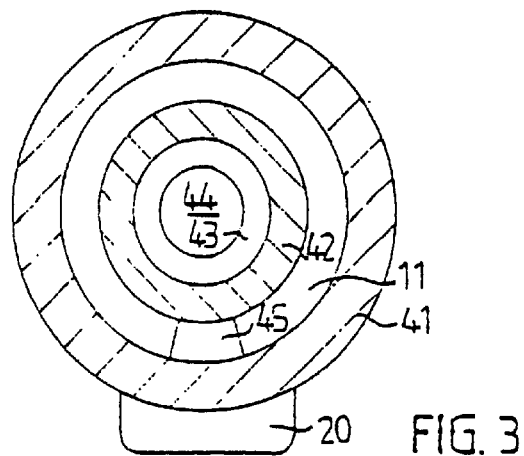
FIG. 3 shows a cross-section through the fastening means of yet another embodiment of the forefoot part.

FIG. 3 shows the same cross-section, along the line II—II in a second embodiment. This second embodiment comprises a remote-controlled motor (not shown) mounted inside the support part 11. As in the first embodiment an outer annular fastening element 41, belonging to the fastening part 20, is adapted to be moved up and down along the support element depending on the motor which is mounted stationary in the support part 11. A second annular fastening element 42 is adapted to move up and down on the inside of the support part 11 depending on the same motor. The two fastening elements 41, 42 are each connected through a joining piece 45, which is arranged to move up and down in a vertical elongated opening (not shown) in the support part 11. The inner annular fastening element 42 cooperates with an intermediate concentrically arranged annular part 43 which has a concentrically arranged threaded circular opening through which opening a rotatable threaded rod 44 passes, which is actively connected to the motor. When such a motor is activated, the threaded rod will rotate and the forefoot part, which is prevented from performing a rotating movement by means of the connecting part 45, will move up and down along, for example, the support part 11.

Figure 4:
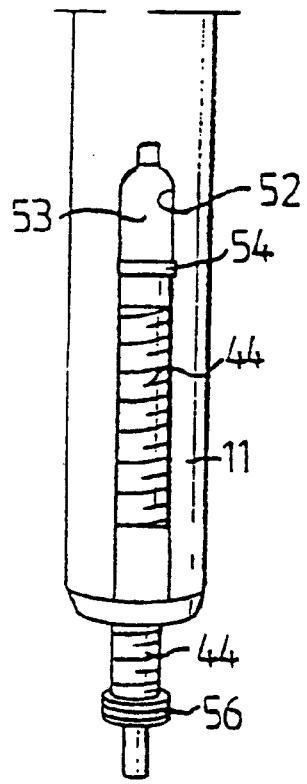
FIG. 4 shows an embodiment of the shape of the support part in a second embodiment.

FIG. 4 shows the support part 11 and the elongated vertical opening 52 (the fastening element 20 and the forefoot part 13 are removed). Through the opening the motor 53 and the threaded rod 44 as well as an elongated part 54 can be seen. The projecting part 54 forms a part of a washer (not shown) on which the motor 53 is mounted. The projecting part 54 prevents the motor from rotating in the support part. The second end 56 of the threaded rod is rotatably fastened to the lower end of the support part 11, e.g. at the heel part. For the sake of clarity the motor is shown in the drawing displaced to the bottom of the tube. Normally the projecting part 54 has a position at the top in the opening 52.

Figure 5:
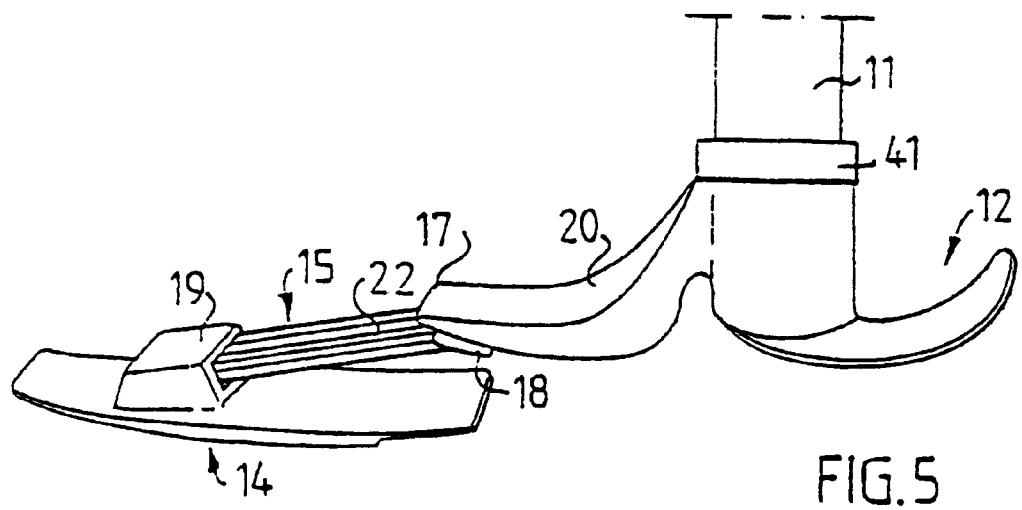
FIG. 5 shows a foot means according to the invention.

FIG. 5 shows a combined forefoot part 13 and heel part 12 according to the invention, where the foot means via the fastening part 20 is arranged on the support part 11 by means of a fastening element 41. The forefoot part 13 comprises a front part 14, an intermediate part 15 and a fastening part 20. The intermediate part 15 forms the part of the forefoot part which is specially shaped in order to be individually adaptable to the individual who is using the prosthesis. In order to achieve this, the intermediate part 15 is arranged in the shape of elongated elastic elements 22 which have a circular, oval or rectangular cross-section.

In one embodiment the intermediate part can be a single element.

The elements 22 are placed on the front part 14 so that the elements 18 are permanently or removably attached in a holder 19. The other end of the element is fastened in a holder 18 (not shown) under the fastening part 20. The holder can be constructed in such a way that the elements can be partially introduced into the holder and thereafter be cut to the right length and subsequently fastened in a permanent manner to the holder and thereby to the fastening part 20.

It is important for the strength of the forefoot part that the elongated elements 18, introduced into the holder which is mounted under the fastening part 20, are fixed in such a way, and that the end of the fastening element 20, under which the holder 18 is mounted, is so shaped that no sharp bending of the elements occurs at the front edge 17 of the fastening part. The front part of the fastening part 20 consequently has a gently bent profile in order to permit the elements to yield.

The material which is chosen for the support part is the usual type of material known within the art.

The forefoot part and the foot means can be manufactured of composite material, injection-moulded plastic etc. with appropriate characteristics and also of metal or the mixture of these materials.

What is claimed is:

1. Adaptable forefoot part for use in a foot prosthesis, comprising:

a front part;

an adjustable and resilient intermediate part comprising at least one elongated element; and a fastening part comprising two essentially concentrically arranged fastening elements adapted to be slidably attached to an elongated support part of a foot prosthesis for locking the forefoot part in a predetermined position; a first fastening element on the outside of the support part and a second inner fastening element on the inside of the support part;

said concentrically arranged fastening elements being joined to each other over a short distance by a connection piece adapted to move up and down in a vertical elongated opening in the support part;

said fastening part extending from the support part towards the front part, and having a first end and a second end;

a first fastening means for fastening a first end of said intermediate part to said front part, whereat said first end of said fastening part is attachable to the support part; and a second fastening means for fastening a second end of said intermediate part to said second end of said fastening part.

2. Adaptable forefoot part according to claim 1, wherein the adjustable and resilient intermediate part comprises several elongated resilient elements having an essentially rectangular, circular, or oval cross-section.

3. System intended for individually adaptable foot prostheses, comprising:

an adaptable forefoot part according to claim 1, a heel part, a support part, and an outer casing of predetermined size.

4. Foot prosthesis for use with a prosthesis socket, comprising:

an elongated support part; and an adaptable forefoot part comprising a front part;

an adjustable and resilient intermediate part comprising at least one elongated element; and a fastening part comprising two essentially concentrically arranged fastening elements adapted to be slidably attached to the elongated support part of the foot prosthesis for locking the forefoot part in a predetermined position; a first fastening element on the outside of the support part and a second inner fastening element on the inside of the support part;

said concentrically arranged fastening elements being joined to each other over a short distance by a connection piece adapted to move up and down in a vertical elongated opening in the support part;

said fastening part extending from the support part towards the front part, and having a first end and a second end;

a first fastening means for fastening a first end of said intermediate part to said front part, whereat said first end of said fastening part is attached to the support part; and a second fastening means for fastening a second end of said intermediate part to said second end of said fastening part.

5. Foot prosthesis according to claim 4, wherein the second inner fastening element is actively connected to a motor arranged in the support part for up and down movement in said support, and the forefoot part is slidably movable in an axial direction along said support part.

6. Foot prosthesis according to claim 4, wherein the adjustable and resilient intermediate part comprises several elongated resilient elements having an essentially rectangular, circular, or oval cross-section.

* * * * *